United States Patent [19]

Evans et al.

[11] 4,311,712

[45] Jan. 19, 1982

[54] PROCESS FOR PREPARING FREEZE-DRIED LIPOSOME COMPOSITIONS

[75] Inventors: John R. Evans; Francis J. T. Fildes; Jean E. Oliver, all of Macclesfield, England

[73] Assignee: Imperial Chemical Industries Limited, London, England

[21] Appl. No.: 67,948

[22] Filed: Aug. 20, 1979

Related U.S. Application Data

[63] Continuation of Ser. No. 889,926, Mar. 24, 1978, abandoned.

[30] Foreign Application Priority Data

May 10, 1977 [GB] United Kingdom ............... 19510/77

[51] Int. Cl.$^3$ ............................................. A61K 47/00
[52] U.S. Cl. ................................................. 424/365
[58] Field of Search ................................ 424/365, 238

[56] References Cited

PUBLICATIONS

Tyrrell et al.—Biochimica et Biophysica Acta vol. 457 (1976) pp. 259–274.

Primary Examiner—Sam Rosen
Attorney, Agent, or Firm—Cushman, Darby & Cushman

[57] ABSTRACT

Process for preparing a freeze-dried, potential liposome, mixture which comprises either (a) dissolving at least one liposome-forming amphipathic lipid, at least one biologically-active compound, and optionally one or more adjuvants, in a suitable solvent, and then freeze-drying the solution, or (b) preparing by any known method an aqueous liposome composition containing at least one biologically-active compound, and then freeze-drying the said aqueous liposome composition. Process for preparing an aqueous liposome composition which comprises dispersing said freeze-dried, potential liposome, mixture, obtained by procedure (a) or (b), in a suitable aqueous medium.

12 Claims, No Drawings

PROCESS FOR PREPARING FREEZE-DRIED LIPOSOME COMPOSITIONS

This is a continuation of application Ser. No. 889,926, filed Mar. 24, 1978, now abandoned.

This invention relates to liposomes and more particularly it relates to improved methods for the manufacture of liposomes.

Liposomes are quite widely described in the literature, and their structure is well known. Usually they have an onion-like multilamellar structure comprising a plurality of phospholipid bilayers spaced one from another by aqueous material. Another type of liposome which is known consists of a single phospholipid bilayer enclosing aqueous material; these unilamellar forms are sometimes referred to as "vesicles". In recent years there has been increasing interest in the use of liposomes as carriers of compounds which are of interest because of one or other biological property, for example medicaments, proteins, enzymes, hormones, vitamins and marker compounds, etc. It is to be understood that this broad group of biologically interesting compounds, which includes medicaments (human and veterinary) but is not restricted thereto, will be referred to in this specification as "biologically active compounds".

The encapsulation of a biologically active compound in liposomes can be achieved by a variety of methods. The method most commonly used involves casting a film of phospholipid (with or without a charged lipid) by evaporation from a solution in an organic solvent, for example chloroform, and then dispersing the film in a suitable aqueous medium. In the case of lipid-soluble biologically active compounds, that is, those which associate with the lipid layers rather than the aqueous phase of the liposomes, the compound is usually cast as a film together with a phospholipid, using a common organic solvent. In the case of water-soluble biologically active compounds the compound is usually encapsulated in liposomes by dispersing a cast phospholipid film with an aqueous solution of the compound. The encapsulated compound is then separated from the free compound by centrifugation, chromatography or some other suitable procedure. In the case of biologically active compounds which associate with the lipid phase of liposomes, provided they are present in an amount below their maximum lipid solubility or below the maximum amount that can be bound by the lipid, liposomes prepared by the above method usually contain most of the compound bound in the lipid bilayers, and separation of the free compound is not so critical as in the case of water-soluble biologically active compounds which do not bind to lipid.

The above-mentioned method does not lend itself to large scale usage. In addition, aqueous liposome dispersions only have limited stability and therefore their storage life is limited. Moreover, the liposomes can aggregate and precipitate as a sediment. Although such sediments can usually be re-dispersed, the structure and size distribution of the original dispersion may be changed. Aggregation and sedimentation can be reduced by the incorporation of charged lipids into the liposomes, but this does not guarantee a satisfactory storage life. The loss of the biologically active compound from the liposome into the external aqueous medium is another factor which restricts the potential of these preparations as practical dosage forms. This is particularly severe for low molecular weight, water-soluble compounds, but lipid-soluble compounds too can partition into the external aqueous medium until equilibrium is reached. If the content of compound is small, and/or the volume of the external aqueous medium is large, this loss can represent a significant proportion of the total content of the biologically active compound in the liposomes.

All of these factors restrict the use of liposomes as practical carriers of biologically active compounds, particularly in medicament therapy. One solution might be to prepare and store the lipid/biologically active compound film, and then disperse the film to form liposomes as needed just before use. However, unit dose film preparation and storage presents serious practical difficulties, and therefore this idea does not provide a practical solution to the problems outlined above. The present invention is concerned with two alternative, but related, methods which do provide a practical solution. In brief, the methods comprise either (1) dissolving the necessary substances in a suitable solvent and then freeze-drying the solution, whereafter the resulting freeze-dried mixture is stored and, when desired, made up into an aqueous liposome preparation, or (2) preparing an aqueous liposome preparation by any known method and then freeze-drying the preparation, whereafter the resulting freeze-dried mixture is stored and, when desired, made up into an aqueous liposome preparation. Any conventional freeze-drying procedure can be used in carrying out either of the freeze-drying methods of this invention. For brevity hereinafter, the expression "freeze-dried, potential liposome, mixtures" will be used for the freeze-dried mixtures obtainable according to this invention which, upon dispersion in a suitable aqueous medium, afford the desired liposome preparations. Unexpectedly, when a freeze-dried, potential liposome, mixture of this invention is re-dispersed in a suitable aqueous medium, for example isotonic saline, liposomes are formed which are similar to those prepared by the known film dispersion method. In the case of a lipid-soluble or lipid-bound biologically active compound, the compound is re-incorporated into the liposomes to a large extent. On the other hand, as explained below, the methods of the invention are not so suitable for those water-soluble biologically active compounds which do not bind to lipid. The freeze-dried mixtures disperse easily when shaken with an aqueous medium, and it appears that they lead to liposome preparations having a narrower size distribution than a corresponding preparation obtained by dispersing a cast film. This might be advantageous as regards the reproducibility of the effect of liposome preparations.

According to the invention there is provided a method for the manufacture of a freeze-dried, potential liposome, mixture which comprises dissolving at least one liposome-forming amphipathic lipid, at least one biologically active compound, and optionally at least one adjuvant in a solvent, and then freeze-drying the solution to produce a freeze-dried, potential liposome, mixture.

Any amphipathic lipid which is known to be suitable for preparing liposomes by known methods can be used in the methods of this invention. Thus a wide variety of lipids may be used according to this invention, but those which are non-immunogenic and bio-degradable are preferred. Examples of suitable lipids are the phospholipids, for example the natural lecithins, for example egg lecithin or soya bean lecithin, or synthetic lecithins, for example saturated synthetic lecithins, for example dimyristoyl-phosphatidylcholine, dipalmitoyl-phosphatidylcholine or distearoyl-phosphatidylcholine, or unsaturated synthetic lecithins, for example dioleyl-phosphatidycholine or dilinoleyl-phosphatidylcholine. Either a single phospholipid or a mixture of phospholipids may be used.

As indicated above, the biologically active compound may be any compound having a property of biological interest. Thus, the compound may be a medicament, protein, enzyme, hormone, vitamin or marker compound, etc. It is to be understood that the methods of this invention are particularly useful in the case of lipid-soluble or lipid-bound biologically active compounds (which include some water-soluble compounds, for example some proteins). The said methods are not so suitable for water-soluble, non-lipid-bound, biologically active compounds, because in those cases only a relatively small fraction of the compound is re-incorporated into the liposomes upon dispersion of the freeze-dried mixture. Nevertheless, this drawback is acceptable provided that a suitable excess of the water-soluble biologically active compound is incorporated into the freeze-dried mixture. Also, when liposomes are prepared from such a mixture, if the presence of free biologically active compound in the external aqueous medium is disadvantageous, the free compound must be removed by one of the above-mentioned methods. Thus, the suitability of the methods of the invention in the case of a water-soluble, non lipid-bound, biologically active compound depends upon all of the relevant facts, including (1) the nature of the compound's activity, (2) the compound's potency, (3) the amount of the compound incorporated in the liposome preparation produced according to this invention, and (4) the desirability or not of the free compound being present in the external aqueous medium.

The optional adjuvants include a substance which provides a negative charge, for example egg phosphatidic acid, dipalmitoyl-phosphatidic acid, dicetyl phosphate or beef brain ganglioside, or a substance which provides a positive charge, for example stearylamine or stearylamine acetate, or a substance which affects the physical properties of the lipid bilayers in the liposomes in some desirable way, for example rendering them more fluid or more rigid, as required, for example cholesterol.

As indicated above, suitable solvents have the property of dissolving the above-mentioned mixture of ingredients. The solvent may consist of one or more substances. Preferred solvents remain solid during the freeze-drying process. Particularly preferred solvents have a melting point which is close to room temperature, for example t-butanol, n-butanol, dioxan, acetic acid, pyridine or piperdine. Optionally, one or more other liquids which aid in dissolving the ingredients, for example water or chloroform, may also be present.

According to a further feature of the invention there is provided the freeze-dried, potential liposome, mixture which is obtainable by the method described immediately above.

According to a further feature of the invention there is provided a method for the manufacture of an aqueous liposome preparation containing at least one biologically active compound, which comprises dispersing a freeze-dried, potential liposome, mixture obtainable by the method described immediately above, in a suitable aqueous medium.

As a suitable aqueous medium there may be mentioned, for example, distilled water, isotonic saline, or a sterile or non-sterile buffer solution.

According to a further feature of the invention there is provided a method for the manufacture of a freeze-dried, potential liposome, mixture, which comprises preparing, by any known method, an aqueous liposome composition comprising at least one biologically active compound, and then freeze-drying the aqueous liposome composition to produce a freeze-dried, potential liposome, mixture.

The details given above concerning suitable lipids, biologically active compounds and adjuvants apply equally to the method defined immediately above.

According to a further feature of this invention there is provided the freeze-dried, potential liposome, mixture which is obtainable by the method described immediately above.

According to a further feature of the invention there is provided a method for the manufacture of an aqueous liposome preparation containing at least one biologically active compound, which comprises dispersing a freeze-dried, potential liposome, mixture, obtainable by the method described immediately above, in a suitable aqueous medium.

Suitable aqueous media are mentioned hereinbefore.

The invention is illustrated but not limited by the following Examples:

EXAMPLE 1

Dipalmitoyl-phosphatidylcholine (hereinafter "DPPC"; 59.6 mg.), $^3$H-cortisol 21-palmitate (hereinafter "$^3$H-CP"; 6.54 mg.) and stearylamine acetate (3.81 mg.) were dissolved in re-distilled t-butanol (3 ml.) at 60° C. The solution was transferred to a 250 ml. round-bottomed flask and frozen as a thin film by immersing and swirling the flask in a freezing mixture of methanol and solid carbon dioxide. The solvent was then removed under vacuum using a commercial freeze-dryer. There was thus obtained a freeze-dried, potential liposome, mixture as a powder which could be stored in sealed containers until required.

Distilled water (10 ml.) was added to the freeze-dried powder, and the resulting mixture was heated to about 70° C. on a water bath. Gentle shaking of the flask caused the powder to disperse, giving a milky suspension which proved to contain liposomes when examined microscopically. Duplicate samples (50 μl.) of the suspension were taken for scintillation counting, to determine the steroid content before washing. The remainder of the suspension was diluted to 25 ml. volume with distilled water, and ultracentrifuged at 120,000 g for 30 min. The liposome plug was dispersed to 10 ml. volume with distilled water, and duplicate samples (50 μl.) of the washed suspension were removed for scintillation counting. Comparison of the counts before and after washing showed that 90% of the steroid remaining in the freeze-dried powder was incorporated into the washed liposomes.

EXAMPLE 2

DPPC (49 mg.) and $^3$H-CP (7 mg.) were dissolved in redistilled t-butanol (5.05 ml.) at 60° C. Duplicate samples (5 μl.) were taken for scintillation counting, and the remaining solution was immediately frozen on the wall of a 250 ml. round-bottomed flask by immersion in a freezing mixture (methanol solid carbon dioxide). The t-butanol was then removed by means of a commercial freeze-dryer. There was thus obtained a freeze-dried, potential liposome, mixture. This mixture was scraped off the flask's wall, and three samples (10, 11 and 12.7 mg.) were weighed into vials. Distilled water (2.5 ml.) was added to each vial, and the mixtures were heated to 50° C. on a water bath. The mixture was then dispersed to form liposomes by vigorous shaking. Duplicate samples (50 µl.) of each liposome preparation were taken for scintillation counting. The liposome preparations were added to dry, weighed ultracentrifuge tubes, diluted to 10 ml. with distilled water, and ultracentrifuged at 120,000 g for 40 min. at 4° C. The supernatant liquids were removed from the lipid plugs, and two of the three plugs were dried in a vacuum oven to a weight representing 50% by weight water content. The third plug was re-suspended in water (2.5 ml.), and duplicate samples (50 µl.) were taken for scintillation counting.

The radioactive counts showed that, after dispersion of the three freeze-dried samples in water, 86±4% of the original steroid was present in the dispersions. Loss of radioactivity was due to the loss of a small fraction of the potential liposome mixture during freeze-drying. After the third sample was washed, 73% of the total steroid remained associated with liposomes.

Duplicate samples (6 mg.) of both dried liposome plugs were then weighed into sample holders for differential scanning calorimetry (hereinafter "DSC"). The DSC spectra of the mixtures between 0° C. and 50° C. were recorded on a Perkin Elmer differential scanning calorimeter. Control samples for DSC were also prepared by mixing the same weights of DPPC and $^3$H—CP as in the original mixture, and then mixing them with 50% by weight of water. These served as "non-liposome" control mixtures. The DSC spectra of these control mixtures were measured as described above.

The DSC spectrum of DPPC alone consists of a main transition endotherm at 41° C. and a pre-transition endotherm at 35° C. The "half-peak" line width of the main endotherm is approximately 3° C. The experiments described above showed that, in the "non-liposome" control mixtures, both peaks were observed in the DSC spectra of the mixtures, and the line width remained at about 3° C. This is believed to show that in simple mixtures (i.e. not liposomes) the steroid does not change the DSC spectrum of the lipid. The spectra of the duplicate liposome preparations showed one transition only (the main endotherm), and the average line width of those preparations was 5.8° C., a considerable broadening compared with the control mixtures. This broadening results from the molecular interaction of the lipid and steroid in the liposomes prepared by the above method. Therefore, there can be no doubt that liposomes prepared by the above method contained the steroid in the liposomes.

EXAMPLE 3

Egg lecithin (16.1 mg.), egg phosphatidic acid (2 mg.) and $^3$H—CP (1.66 mg.) were dissolved in chloroform (5 ml.), and the solution was poured into a 250 ml. round-bottomed flask. The solvent was removed at room temperature by rotating the flask and blowing a stream of dry nitrogen into it. The lipid film thereby obtained was then dispersed at room temperature in water (5 ml.), giving a liposome preparation. Duplicate samples (50 µl.) were removed for scintillation counting. The remainder of the liposome preparation was diluted to 25 ml. with distilled water in an ultracentrifuge tube, and ultracentrifuged at 120,000 g for 30 mins. The supernatant liquid was removed from the liposome plug, and the plug was dispersed in distilled water (5 ml.). Duplicate samples (50 µl.) of this dispersion were taken, and the steroid incorporation was measured by scintillation counting. The remainder of the liposome dispersion was frozen, using a methanol-solid carbon dioxide mixture, and the solvent removed using a commercial freeze-dryer. There was thus obtained a freeze-dried, potential liposome, mixture.

The freeze-dried mixture was stored for five days, and to it was then added 0.9% w/v saline (5 ml.). Liposomes were formed by gently shaking the mixture in a flask at room temperature. Microscopic examination confirmed the presence of liposomes. Two days later the liposomes were washed twice with 0.9% w/v saline by the method described above, except that saline was used instead of water. The steroid content of the liposomes was determined by scintillation counting. Comparison of the radioactivity of the dispersions before and after freeze-drying showed that 72% of the steroid present in the washed preparation before freeze-drying was retained in the washed liposomes formed after freeze-drying.

EXAMPLE 4

DPPC (29.8 mg.) and $^3$H—CP (3.32 mg.) were dissolved in chloroform (5 ml.) and cast as a thin film on the wall of a 250 ml. round-bottomed flask by evaporating the solvent at room temperature using a stream of dry nitrogen. Distilled water (10 ml.) was then added to the flask, and the mixture was heated to 70° C. on a water bath. Liposomes were formed by agitating the hot mixture on a bench vibromixer. Duplicate samples (50 µl.) of the resulting dispersion were removed for scintillation counting. The remainder of the dispersion was washed twice by diluting to 25 ml. with distilled water and ultracentrifugation at 120,000 g for 30 min. The washed liposome plug was re-dispersed in distilled water (10 ml.), and duplicate samples (50 µl.) were taken for scintillation counting. This dispersion (5 ml.) was frozen in a freezing mixture consisting of methanol and solid carbon dioxide, and the solvent was removed under vacuum using a commercial freeze-dryer. There was thus obtained a freeze-dried, potential liposome, mixture which was stored until required.

Distilled water (5 ml.) was added to the freeze-dried mixture, and the resulting mixture was heated to 70° C. on a water bath, and gently shaken. Microscopic examination of the resulting milky suspension showed it to consist of a suspension of liposomes, with a narrow size distribution. This suspension was ultracentrifuged at 120,000 g for 30 min., and the liposome plug was then re-dispersed in distilled water (5 ml.). Duplicate samples (50 µl.) of the resulting suspension were taken for assaying the final steroid content of the liposome Scintillation counting showed that 78% of the steroid incorporated in the original washed dispersion was present in the final washed liposome preparation formed from the freeze-dried mixture.

DSC (see Example 2) on the liposomes prepared from the original film and those prepared from the freeze-dried mixture showed that the lipid transition endotherm was broadened by the steroid in the liposomes, and that this broadening was maintained after the freeze-dried mixture was dispersed in distilled water. This proved that the steroid was incorporated into the final liposomes prepared from the freeze-dried mixture.

EXAMPLE 5

All of the procedures described in this Example were carried out in a sterile room (sterilised with formaldehyde, and then purged with sterile air) using convential aseptic precautions. The freeze-dryer (Edwards Speedivac Centrifugal freeze-dryer, model 5PS) was sterilised with formaldehyde and then purged with sterile air. The other apparatus used was either sterilised by dry heat or by autoclaving.

DPPC (697.2 mg.), dipalmitoyl-phosphatidic acid (99.6 mg.) and cortisol 21-palmitate (99.6 mg.) were dissolved at 60° C. in re-distilled t-butanol (60 ml.). The hot solution was immediately sterilised by passage through a 0.22 μ. 'MF-millipore' filter (Millipore Corporation, Bedford, MA, USA) maintained at a temperature of 50° C.; this passage was carried out twice. 2 ml. aliquots of the sterile solution were placed in 5 ml. sterile multi-dose vials. The contents of the vials were freeze-dried using the above-mentioned freeze-dryer, and each vial was then sealed using a sterile rubber closure and a metal, multi-dose cap. There were thus obtained sealed samples of a sterile, freeze-dried, potential liposome, mixture.

A sterile 0.9% w/v aqueous solution of sodium chloride was introduced into one of the above-mentioned sealed vials, which was then heated to 50° C. on a water bath, and shaken vigorously. There was thus obtained a sterile liposome preparation which was suitable for administration by injection.

EXAMPLE 6

Egg lecithin (15 mg.), cholesterol (2.09 mg.) and dicetyl phosphate (1.55 mg.) were dissolved in chloroform (5 ml.), and cast as a thin film on the wall of a test tube. $^{125}$I-Angiotensin II (0.1 mg.) in 3.3 mM phosphate buffer (pH 7.4; 1 ml.) was added to the tube. The lipid was dispersed in the aqueous medium with the aid of a bench vibromixer to form liposomes. The liposome dispersion was washed twice by diluting to 26 ml. with 3.3 mM phosphate buffer (pH 7.4), followed by ultracentrifugation at 120,000 g for 1 hr. The washed liposome plug was redispersed in 3.3 mM phosphate buffer (pH 7.4; 5 ml.) and duplicate samples (0.25 ml.) were removed for scintillation counting. 4 ml. of the remaining suspension were placed in a test tube, frozen (methanol-solid carbon dioxide), and freeze-dried. The resulting freeze-dried, potential liposome, mixture was resuspended in 3.3 mM phosphate buffer (pH 7.4; 2 ml.) and washed twice as before. The washed liposome plug was resuspended in 3.3 mM phosphate buffer (pH 7.4; 4 ml.). Duplicate samples (0.25 μl.) were removed for scintillation counting. 26% of the initial amount of angiotensin II was retained in the liposomes after the first liposome preparation and washing. 28% of this 26%, that is 7% of the initial amount of angiotensin II, was retained in the liposomes after freeze-drying and reconstitution.

The 3.3 mM phosphate buffer (pH 7.4) used in this Example and Example 7 was prepared by dissolving potassium dihydrogen phosphate (0.895 g.) and disodium hydrogen phosphate dihydrate (4.765 g.) in distilled water, and making the solution up to 1 liter with distilled water.

EXAMPLE 7

Egg lecithin (15 mg.), cholesterol (2.09 mg.) and dicetyl phosphate (1.55 mg.) were dissolved in chloroform (5 ml.), and cast as a thin film on the wall of a test tube. $^{3}$H-Inulin (5 mg.) in 3.3 mM phosphate buffer (pH 7.4; 1 ml.) was added to the tube. The lipid was dispersed in the inulin solution with the aid of bench vibromixer to form liposomes. The liposome dispersion was washed twice by diluting to 26 ml. with 3.3 mM phosphate buffer (pH 7.4), followed by ultracentrifugation at 120,000 g for 1 hr. The washed liposome plug was redispersed in 3.3 mM phosphate buffer (pH 7.4; 2.1 ml.), and duplicate samples (1 μl.) were removed for scintillation counting. The remaining suspension was frozen (methanol-solid carbon dioxide mixture) and freeze-dried in a test tube. The resulting freeze-dried, potential liposome, mixture was resuspended in 3.3 mM phosphate buffer (pH 7.4; 1 ml.) to form liposomes and washed twice as before. The washed liposome plug was resuspended in 3.3 mM phosphate buffer (pH 7.4; 2 ml.), and duplicate samples (1 μl.) were taken for scintillation counting. 21% of the initial amount of inulin was retained in liposomes after the first liposome preparation and washing. 17% of this 21%, that is 4% of the initial amount of inulin, was retained in the liposomes after freeze-drying and reconstitution.

What we claim is:

1. A method for the manufacture of a freeze-dried, potential liposome, mixture which comprises dissolving at least one liposome-forming amphipathic lipid and at least one lipid-soluble or lipid-bound biologically active compound in an organic solvent which remains solid during the freeze-drying process, and then freeze-drying the solution to produce a freeze-dried, potential liposome, mixture.

2. The method claimed in claim 1 in which the lipid is a natural or synthetic lecithin.

3. The method claimed in claim 1 in which the biologically active compound is a medicament.

4. The method claimed in claim 1 in which there is present at least one adjuvant selected from the group consisting of cholesterol, substances which provide a negative charge, and substances which provide a positive charge.

5. The method claimed in claim 1 in which the solvent has a melting point close to room temperature.

6. A new composition of matter which is the freeze-dried, potential liposome, mixture obtained as the product of the method claimed in claim 1.

7. The method claimed in claim 1 in which the solvent is a member selected from the group consisting of t-butanol, n-butanol, dioxan, acetic acid, pyridine and piperidine.

8. A method for the manufacture of an aqueous liposome preparation containing at least one lipid-soluble or lipid-bound biologically active compound, which comprises dispersing a freeze-dried, potential liposome, mixture in a suitable aqueous medium, the said freeze-dried, potential liposome, mixture being obtained by dissolving at least one liposome-forming amphipathic lipid and at least one lipid-soluble or lipid-bound biologically active compound in an organic solvent which remains solid during the freeze-drying process, and then freeze-drying the resulting solution.

9. An aqueous liposome preparation containing at least one lipid-soluble or lipid-bound biologically active compound, obtained by a method as claimed in claim 8.

10. The method claimed in claim 8 in which the biologically active compound is a medicament.

11. The method claimed in claim 8 in which there is present at least one adjuvant selected from the group consisting of cholesterol, substances which provide a negative charge, and substances which provide a positive charge.

12. An aqueous liposome preparation containing at least one lipid-soluble or lipid-bound biologically active compound, obtained by a method as claimed in claim 11.

* * * * *